US012582553B2

(12) United States Patent
Katchinskiy et al.

(10) Patent No.: US 12,582,553 B2
(45) Date of Patent: Mar. 24, 2026

(54) SPATIAL LIGHT MODULATION TARGETING OF THERAPEUTIC LASERS FOR TREATMENT OF OPHTHALMOLOGICAL CONDITIONS

(71) Applicant: Pulsemedica Corp., Edmonton (CA)

(72) Inventors: Nir Katchinskiy, Edmonton (CA); Abdulhakem Elezzabi, Edmonton (CA)

(73) Assignee: Pulsemedica Corp., Edmonton (CA)

( * ) Notice: Subject to any disclaimer, the term of this patent is extended or adjusted under 35 U.S.C. 154(b) by 0 days.

(21) Appl. No.: 18/648,162

(22) Filed: Apr. 26, 2024

(65) Prior Publication Data

US 2024/0366427 A1 Nov. 7, 2024

Related U.S. Application Data

(63) Continuation of application No. 18/545,359, filed on Dec. 19, 2023, now Pat. No. 11,992,440, which is a continuation of application No. 18/249,009, filed as application No. PCT/CA2021/051659 on Nov. 23, 2021, now Pat. No. 12,343,289.

(30) Foreign Application Priority Data

Nov. 24, 2020 (CA) ................................. CA 3100460

(51) Int. Cl.
A61F 9/008 (2006.01)
A61B 3/10 (2006.01)
A61B 17/00 (2006.01)

(52) U.S. Cl.
CPC .............. *A61F 9/008* (2013.01); *A61B 3/102* (2013.01); *A61B 2017/00159* (2013.01); *A61F 2009/00851* (2013.01)

(58) Field of Classification Search
CPC ........... A61B 2017/00159; A61B 3/102; A61F 2009/00846; A61F 2009/00851; A61F 2009/00897; A61F 9/008; A61F 9/00802; A61F 9/00821; A61F 9/00825
See application file for complete search history.

(56) References Cited

U.S. PATENT DOCUMENTS

| | | | |
|---|---|---|---|
| 7,805,009 B2 | 9/2010 | Everett et al. | |
| 7,980,696 B1 | 7/2011 | Taki | |
| 9,550,069 B1 | 1/2017 | Elezzabi | |
| (Continued) | | | |

FOREIGN PATENT DOCUMENTS

| | | | |
|---|---|---|---|
| CA | 2714116 A1 | 8/2009 | |
| CA | 3096285 A1 | 4/2022 | |
| (Continued) | | | |

OTHER PUBLICATIONS

Gomez, A., et al., "Image Reconstruction in a Manifold of Image Patches: Application to Whole-Fetus Ultrasound Imaging", Machine Learning for Medical Image Reconstruction, Oct. 24, 2019, pp. 226-235.

(Continued)

*Primary Examiner* — Scott Luan

(74) *Attorney, Agent, or Firm* — Perkins Coie LLP

(57) ABSTRACT

A therapeutic laser for use in treating ophthalmological conditions can be modulated by a spatial light modulation device in order to focus the therapeutic laser on a plurality of target locations simultaneously.

19 Claims, 4 Drawing Sheets

(56) References Cited

U.S. PATENT DOCUMENTS

| 10,117,576 B2 | 11/2018 | de Boer |
| 10,694,939 B2 | 6/2020 | Kuo |
| 2004/0174495 A1 | 9/2004 | Levine |
| 2004/0254567 A1 | 12/2004 | Holz et al. |
| 2007/0046948 A1 | 3/2007 | Podoleanu |
| 2007/0115481 A1 | 5/2007 | Toth et al. |
| 2009/0093798 A1 | 4/2009 | Charles |
| 2010/0094135 A1 | 4/2010 | Fang-Yen |
| 2010/0182610 A1 | 7/2010 | Utsunomiya |
| 2010/0290007 A1 | 11/2010 | Van de Velde |
| 2011/0009779 A1 | 1/2011 | Romano et al. |
| 2011/0043661 A1 | 2/2011 | Podoleanu |
| 2011/0058175 A1 | 3/2011 | Suehira |
| 2011/0134436 A1 | 6/2011 | Podoleanu |
| 2011/0234978 A1 | 9/2011 | Hammer et al. |
| 2011/0301508 A1 | 12/2011 | Sethuraman et al. |
| 2012/0002164 A1 | 1/2012 | Yamamoto |
| 2012/0154747 A1 | 6/2012 | Makihira |
| 2012/0165799 A1 | 6/2012 | Yamamoto |
| 2012/0274904 A1 | 11/2012 | Saito |
| 2012/0294500 A1 | 11/2012 | Utsunomiya |
| 2013/0286348 A1 | 10/2013 | Makihira |
| 2014/0104618 A1 | 4/2014 | Potsaid |
| 2014/0194860 A1 | 7/2014 | Dick et al. |
| 2015/0116664 A1 | 4/2015 | Uchida |
| 2015/0141972 A1 | 5/2015 | Woodley |
| 2015/0305617 A1 | 10/2015 | Tachikawa et al. |
| 2016/0022490 A1 | 1/2016 | Ergun et al. |
| 2016/0074221 A1 | 3/2016 | Tassignon |
| 2016/0250067 A1 | 9/2016 | Iwata |
| 2016/0284103 A1 | 9/2016 | Huang |
| 2017/0007112 A1 | 1/2017 | Gonzalez |
| 2017/0035291 A1 | 2/2017 | Jiao |
| 2017/0132826 A1 | 5/2017 | Grady et al. |
| 2017/0189228 A1 | 7/2017 | Yang |
| 2017/0310901 A1 | 10/2017 | Sheikh et al. |
| 2017/0360411 A1 | 12/2017 | Rothberg et al. |
| 2018/0101644 A1 | 4/2018 | Hammes et al. |
| 2018/0111008 A1 | 4/2018 | Chapuis et al. |
| 2018/0116502 A1 | 5/2018 | Ishinabe |
| 2018/0200112 A1 | 7/2018 | Krampert |
| 2018/0271362 A1 | 9/2018 | Palczewski |
| 2018/0344150 A1 | 12/2018 | Bajraszewski |
| 2018/0353064 A1 | 12/2018 | Soetikno et al. |
| 2019/0000316 A1 | 1/2019 | Hirose |
| 2019/0038766 A1* | 2/2019 | Mohanty ................ A61K 41/00 |
| 2019/0099291 A1 | 4/2019 | Herekar et al. |
| 2019/0114804 A1 | 4/2019 | Sundaresan et al. |
| 2019/0125178 A1 | 5/2019 | Murata |
| 2019/0130580 A1 | 5/2019 | Chen et al. |
| 2019/0188851 A1 | 6/2019 | Zouridakis |
| 2019/0278972 A1 | 9/2019 | Anderson |
| 2019/0332900 A1 | 10/2019 | Sjolund et al. |
| 2019/0339356 A1 | 11/2019 | Schildknecht et al. |
| 2020/0015675 A1 | 1/2020 | Shibutani |
| 2020/0160301 A1 | 5/2020 | Lyman et al. |
| 2020/0194108 A1 | 6/2020 | Podilchuk et al. |
| 2020/0218943 A1 | 7/2020 | Osake |
| 2020/0242768 A1 | 7/2020 | Ashok |
| 2020/0245960 A1 | 8/2020 | Richter et al. |
| 2020/0250436 A1 | 8/2020 | Lee et al. |
| 2020/0285906 A1 | 9/2020 | Do et al. |
| 2020/0288973 A1 | 9/2020 | Ono |
| 2020/0294654 A1 | 9/2020 | Harzig et al. |
| 2021/0045672 A1 | 2/2021 | Jia et al. |
| 2021/0142487 A1 | 5/2021 | Xu et al. |
| 2021/0186753 A1 | 6/2021 | Al-Qaisi et al. |
| 2021/0202062 A1 | 7/2021 | Gray |
| 2021/0224997 A1 | 7/2021 | Kushida et al. |
| 2022/0117780 A1 | 4/2022 | Zhang |
| 2022/0151483 A1 | 5/2022 | Ono |
| 2022/0390369 A1 | 12/2022 | Piestun |
| 2023/0372153 A1 | 11/2023 | Katchinskiy |
| 2024/0016660 A1 | 1/2024 | Katchinskiy |

FOREIGN PATENT DOCUMENTS

| CA | 3157811 A1 | 11/2023 |
| CN | 109938919 A | 6/2019 |
| CN | 114511738 A | 5/2022 |
| CN | 117788881 A | 3/2024 |
| EP | 1401326 A2 | 3/2004 |
| EP | 2403603 B1 | 7/2014 |
| FR | 3121535 A1 | 10/2022 |
| JP | 2015195923 A | 11/2015 |
| JP | 2017184874 A | 10/2017 |
| KR | 1020190130310 A | 11/2019 |
| WO | 2016011045 A1 | 1/2016 |
| WO | 2020/020809 A1 | 1/2020 |
| WO | 2020012841 A1 | 1/2020 |
| WO | 2020058459 A1 | 3/2020 |
| WO | 2020/215359 A1 | 10/2020 |
| WO | 2020/227661 A1 | 11/2020 |
| WO | 2021029231 A1 | 2/2021 |
| WO | 2021069168 A1 | 4/2021 |
| WO | 2021069220 A1 | 4/2021 |
| WO | 2021/122762 A1 | 6/2021 |
| WO | 2022077117 A1 | 4/2022 |
| WO | 2022133590 A1 | 6/2022 |
| WO | 2023065042 A1 | 4/2023 |

OTHER PUBLICATIONS

Kaplan, S., et al., "Contrastive Learning for Generating Optical Coherence Tomography Images of the Retina"; Simulation and Synthesis in Medical Imaging, Sep. 21, 2022, pp. 112-121.
International Search Report for International Application No. PCT/CA2021/051451, mailed Dec. 20, 2021, 4 pages.
International Search Report for International Application No. PCT/CA2021/051659, mailed Jan. 27, 2022, 2 pages.
Non-Final Office Action on related U.S. Appl. No. 18/475,558, dated Nov. 7, 2023.
Tam, Johnny and Yang, Qiang; "Optics Retinal Imaging with Eye Tracking"; found at: Adaptive Optics Retinal Imaging with Eye Tracking, National Institute of Biomedical Imaging and Bioengineering (nih.gov).
International Search Report and Written Opinion of corresponding PCT Application No. PCT/CA2022/051556; ISA/CA; Dec. 30, 2022; 11 pages.
International Search Report and Written Opinion of corresponding PCT Application No. PCT/CA2022/051638; ISA/CA; Canadian Intellectual Property Office; Feb. 24, 2023; 8 pages.
International Search Report and Written Opinion of corresponding PCT Application No. PCT/CA2022/051734; ISA/CA; Canadian Intellectual Property Office; Feb. 28, 2023; 16 pages.
Notice of Allowance on related U.S. Appl. No. 18/475,558, dated Apr. 19, 2024.

* cited by examiner

100
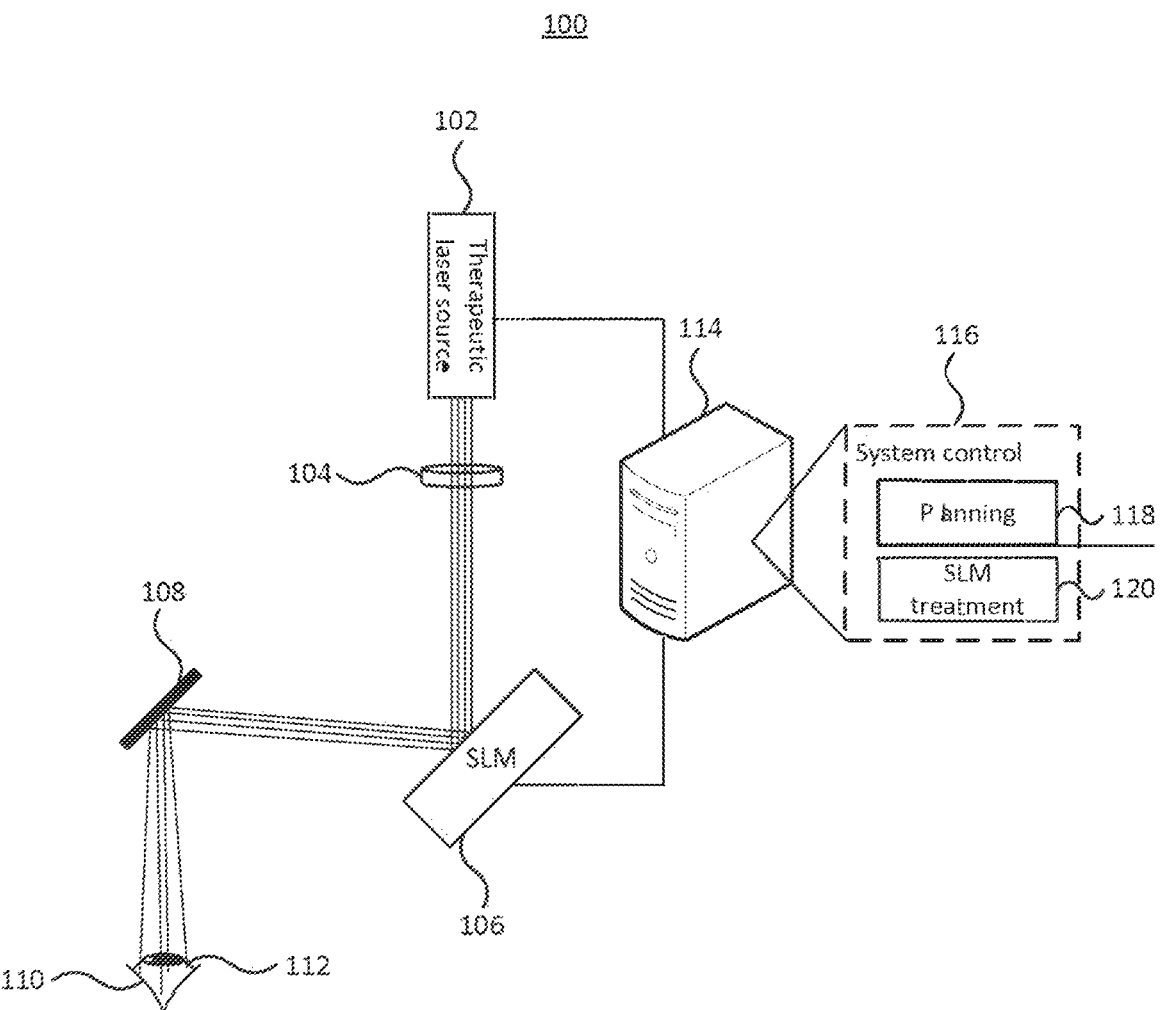
FIG.    1

200
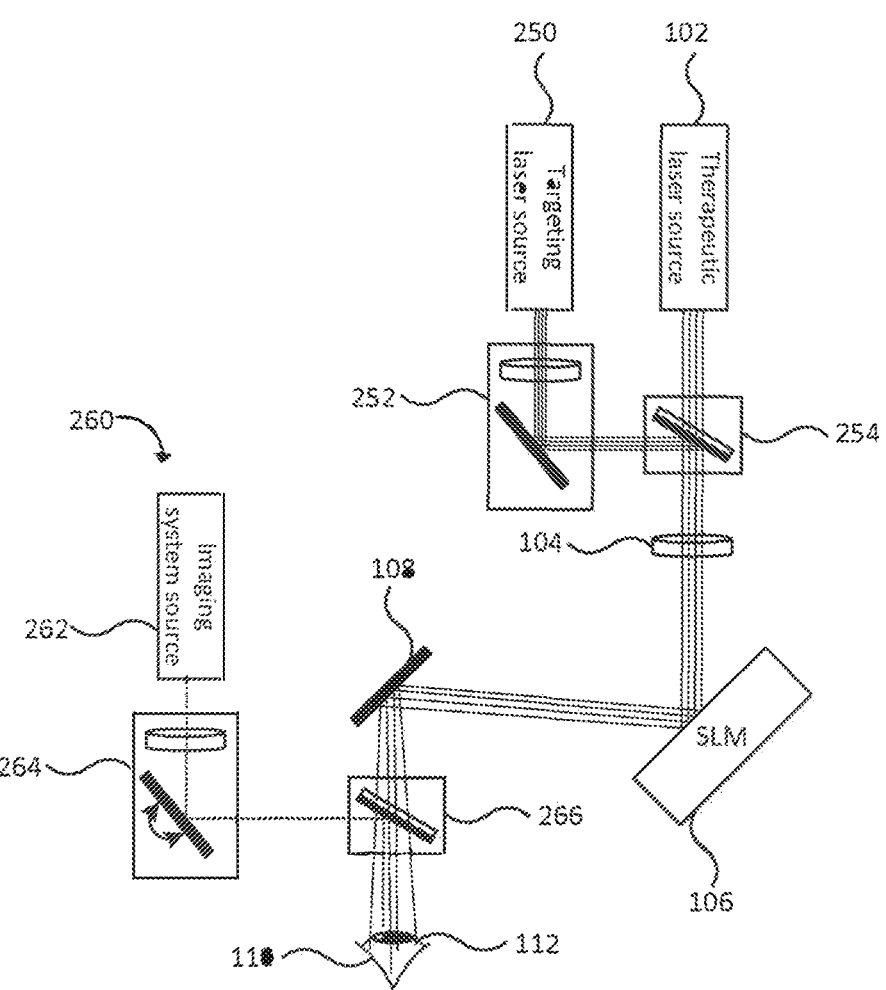
FIG.    2

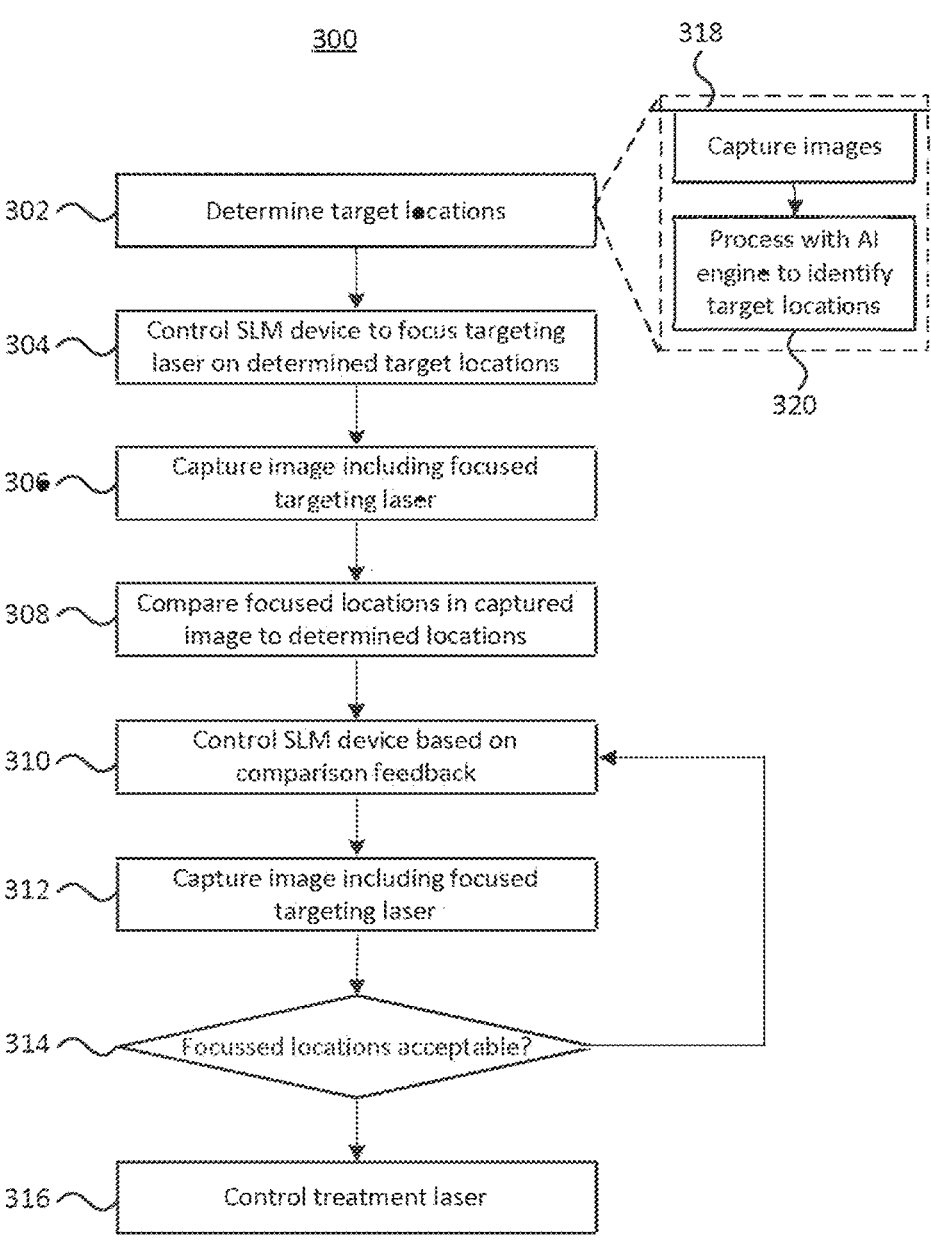
FIG.    3

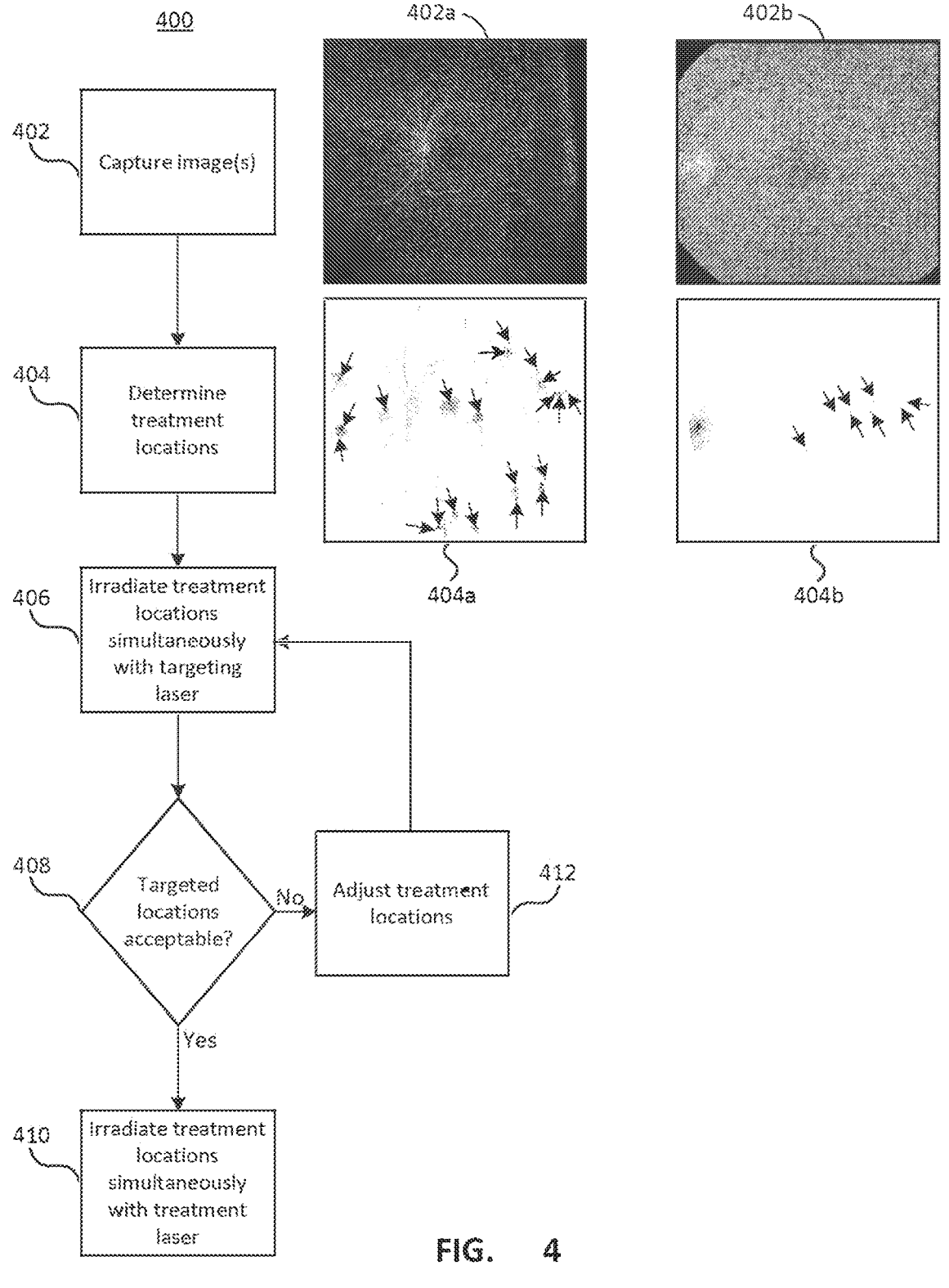
FIG.    4

SPATIAL LIGHT MODULATION TARGETING OF THERAPEUTIC LASERS FOR TREATMENT OF OPHTHALMOLOGICAL CONDITIONS

CROSS-REFERENCE TO RELATED APPLICATIONS

This application is a continuation of U.S. patent application Ser. No. 18/545,359, filed Dec. 19, 2023, which is a continuation of U.S. patent application Ser. No. 18/249,009, filed Apr. 13, 2023, which is the National Stage of International Application No. PCT/CA2021/051659, filed Nov. 23, 2021, and which claims priority to Canadian Patent Application 3,100,460 filed Nov. 24, 2020 and titled "Spatial Light Modulation Targeting of Therapeutic Lasers for Treatment of Ophthalmological Conditions," the entire contents of which are incorporated herein by reference in their entirety.

TECHNICAL FIELD

The current disclosure relates to laser delivery systems for ophthalmology and in particular to targeting of the laser for delivery to one or more target locations.

BACKGROUND

Ophthalmological conditions, including for example, diabetic retinopathy, age-related macular degeneration, vitreomacular traction, tears, retinal detachments, holes, glaucoma, vein occlusion, choroidal detachment, diabetic macular edema, posterior vitreous detachment, cataract, and floaters may include treatment options in which a laser is focused on one or more locations. The delivered/focused laser light is absorbed by the tissue eye which causes some change in the eye, such as photocoagulation, incisions in the tissue, ablation, etc. While laser treatment may be used to treat various eye conditions, the treatment process can often require laser treatment at multiple different locations.

Delivering/focusing a treatment laser to each treatment location can be time consuming, and can requiring precise tracking of the eye to ensure any eye movement is accounted for during the delivery of the laser light. Further, laser treatment at one location may change or affect other treatment locations which may necessitate re-planning the treatment. Further still the laser treatment can be uncomfortable for patients and so treating each target location individually can be undesirable.

Masking techniques have been used to filter treatment laser light and target a plurality of treatment locations simultaneously. However, the masking can present problems with focusing at each individual target location. Further, the masking can be difficult to arrange and align in relation to the patient.

An additional, new and/or improved systems and methods of targeting therapeutic lasers for treatment of ophthalmological conditions is desirable.

SUMMARY

In accordance with the present disclosure there is provided a therapeutic laser delivery system for ophthalmology comprising: a therapeutic laser delivery optical path comprising at least one input port for receiving therapeutic laser light and an output port for delivering at least a portion of the therapeutic laser light to an ophthalmological target; a spatial light modulator (SLM) device arranged to modulate the therapeutic laser light delivered to the ophthalmological target to control target locations of the ophthalmological target the therapeutic laser light is delivered/focused at; and at least one processor configured to determine the target locations and control the SLM device to modulate the therapeutic laser light to be delivered/focused on the determined target locations.

In a further embodiment of the system, the system further comprises: a targeting laser delivery optical path for delivering targeting laser light to the ophthalmological target, wherein the SLM device is further arranged to modulate the targeting laser light to deliver/focus at the target locations of the ophthalmological target.

In a further embodiment of the system, the laser delivery optical path comprises an alignment optical path for aligning and inputting the targeting laser light to the at least one input port of the therapeutic laser delivery optical path.

In a further embodiment of the system, further comprises an imaging system capturing an image of the ophthalmological target.

In a further embodiment of the system, the image captured by the imaging system captures the targeting laser light focused by the SLM device.

In a further embodiment of the system, the captured image is processed to compare the captured targeting laser light focused by the SLM device to the target locations.

In a further embodiment of the system, the comparison of the targeting laser light captured in the image to the target location is used as feedback for controlling the SLM device.

In a further embodiment of the system, the imaging system comprises one or more of: a fundus camera system; a scanning laser ophthalmoscopy (SLO) imaging system; and an optical coherence tomography system.

In a further embodiment of the system, the imaging system comprises a tracking system for tracking eye movement.

In a further embodiment of the system, the determined target locations comprise a plurality of simultaneous treatment locations for the therapeutic laser light.

In a further embodiment of the system, the SLM device is controlled to deliver/focus a portion of the therapeutic laser light on each of the plurality of simultaneous treatment locations at the same time.

In a further embodiment of the system, the portion of the therapeutic laser light delivered/focused on each of the simultaneous treatment locations has a respective power.

In a further embodiment of the system, the respective power of the portion of the therapeutic laser light delivered/focused on at least one of the simultaneous treatment locations differs from the respective power of at least one other one of the simultaneous treatment locations.

In a further embodiment of the system, the at least one processor is further configured to control the SLM device to shape a pulse of the therapeutic laser light.

In a further embodiment of the system, the SLM device comprises one or more of: a liquid crystal-based SLM device; and a microelectromechanical micromirror-based SLM device; a membrane mirror-based SLM device; and an active or a passive metasurface.

In a further embodiment of the system, the target locations of the ophthalmological target are located in one or more of: a sclera of the ophthalmological target; an iris of the ophthalmological target; a pupil of the ophthalmological target; a cornea of the ophthalmological target; a retina of the ophthalmological target; and a vitreous humour of the ophthalmological target.

In a further embodiment of the system, the delivery/focusing of the therapeutic laser at the target locations is used to treat one or more of: diabetic retinopathy; age-related macular degeneration; vitreomacular traction; tears; retinal detachments; holes; glaucoma; vein occlusion; choroidal detachment; diabetic macular edema; posterior vitreous detachment; cataracts; floaters; and dry eye.

In accordance with the present disclosure there is provided a method of targeting a therapeutic laser on an ophthalmological target comprising: determining a plurality of target locations of the ophthalmological device; controlling a spatial light modulation (SLM) device to focus a targeting laser at each of the plurality of determined target locations; capturing an image of the targeting laser focused at the plurality of determined target locations; comparing locations of the focused targeting laser captured in the image to the determined target locations; and controlling the SLM device based on feedback from the comparison of the locations of the focused targeting laser captured in the image to the determined target locations.

In a further embodiment of the method, determining the plurality of target locations comprises: capturing one or more images of the ophthalmological target; and processing the one or more images to determine the plurality of target locations.

BRIEF DESCRIPTION OF THE DRAWINGS

Further features and advantages of the present disclosure will become apparent from the following detailed description, taken in combination with the appended drawings, in which:

FIG. 1 depicts an ophthalmological system for focusing a treatment laser;

FIG. 2 depicts a further ophthalmological system for focusing a treatment laser;

FIG. 3 depicts a method of targeting a therapeutic laser on an ophthalmological target; and FIG. 4 depicts a further method of targeting a therapeutic laser on an ophthalmological target.

DETAILED DESCRIPTION

A treatment laser for ophthalmological can be delivered and/or focused by a spatial light modulation (SLM) device, which allows the treatment laser to be delivered and/or focused on a plurality of locations simultaneously. For example, the treatment laser may be delivered to or focused at a number of different locations to ablate, incise, and/or photocoagulate the tissue. The laser light does not need to be focused and instead may be delivered to the eye, such as for trans scleral light-mediated bio stimulation of the trabecular plates of a patient's eye, which may be used in a treatment for glaucoma or ocular hypertension. The SLM device allows multiple locations to be treated simultaneously. Laser treatment can be painful to individuals and as such it can be beneficial to reduce the number of treatments required. Delivering and/or focusing the treatment laser on multiple locations simultaneously allows treatment to be carried out at once without requiring multiple laser treatments. Previous techniques have treated individual locations sequentially, which requires tracking for eye movement between the individual treatments. Treating multiple locations simultaneously can reduce the amount of eye tracking required and so reduce possible errors in the treatment. Further, laser treatment of individual locations can affect other locations and as such may require re-assessing treatment locations after an individual treatment. In contrast, treating a plurality of locations simultaneously can treat all of the locations without requiring further reassessment. In addition to delivering/focusing the treatment laser at multiple locations, the SLM device is able to control the shape, lightwave phase, lightwave polarization, wavefront tilt, diffraction, wavefront helicity, orbital angular momentum order, and generating non-diffractive light beams (e.g. Bessel and self-healing light beams) of the delivered and/or focused treatment laser.

FIG. 1 depicts an ophthalmological system for delivering/focusing a treatment laser. The system 100 comprises a therapeutic laser source 102 that provides a source for laser light used in the ocular treatment. The therapeutic laser source 102 may be provided by a range of different laser sources including for example a femtosecond laser. The therapeutic laser can be coupled to an optical path that may include one or more optical components depicted schematically by lens 104. The optical components may include for example optical lenses, mirrors, filters, beam splitters, gratings, polarizers, etc. The system 100 further includes an electronically-addressable SLM device 106 that can controllably modulate the light from the therapeutic light source. The SLM device 106 may be for example a liquid crystal based SLM device, such as a liquid crystal on silicon (LCoS) device capable of controllably modulating the phase of the laser light on a pixel by pixel basis. For example an LCOS SLM may comprise a panel of pixel elements, such as 1920×1080, 3840×2160 although other dimensions are possible, that each can be controlled to modulate the phase of impinging light. The SLM device may be controlled in various ways. For example, the SLM device may be driven by electrical signal similar to that used to drive an LCD panel. Although the above described a liquid crystal-based SLM device, other SLM devices may be employed. For example, the SLM device may be provided by a micromirror based SLM device. The SLM device allows the pixel by pixel modulation of the phase of the incident laser light, which allows the pattern of the delivered/focused laser light at the ocular target to be controlled. The SLM device is digitally controllable to impart some form of spatially varying phase modulation on a beam of light that is reflected from it or transmitted through it.

The system 100 may further comprise additional optical components for delivering the modulated laser light to the optical target. The additional optical components are depicted schematically as mirror 108, however may include additional optical components including for example lenses, filters, polarizers, etc. The optical target is a patient's eye 110. The SLM device allows the laser light to be delivered/focused at multiple target locations, one of which is labelled as location 112. The target locations 112 at which the laser light is delivered/focused are locations that have been determined for treatment. For example, in treating age related macular degeneration, the target locations may be the locations of drusen under the retina. Treatment of other ocular conditions may have different targets; however, regardless of what the particular targets are, the SLM device is able to modulate the laser light such that the laser light is simultaneously delivered/focused at a plurality of the target locations.

Although depicted and described as being an individual location, the target locations do not need to be limited to an individual point. The SLM device may deliver/focus the laser light in a determined shape. For example, in treating vitreo macular traction, the shape of the delivered/focused laser light may be a cupped surface or other similar shape that severs the strands causing the traction. Another example, is the treatment of glaucoma where the laser light is delivered to a limbal area of an eye. Here, the delivered laser spot is spatially-configured into specific shapes to irradiate a trabecular meshwork of the eye.

The system 100 further includes one or more controllers, depicted schematically as a computer 114 that controls the system components, including the SLM device and possibly the therapeutic laser source. The one or more controllers may be configured to provide system control functionality 116. The one or more controllers may be configured for example by executing instructions stored in a memory. The system control functionality 116 may include planning functionality 118 that allows the treatment to be planned. The planning functionality 118 may be provided in a wide variety of ways, from for example a manual process that allows a user to load images of the patient's eye and specify the target locations on the images. Additionally, or alternatively, the planning functionality may process the images to automatically, or semi-automatically, identify the target locations. The processing may be based on a specified ocular condition to be treated, or may determine an ocular condition present in the image or images, and determine the treatment locations for treating the condition. In addition to planning the treatment locations, the planning functionality may also determine or specify the parameters of the treatment at each location, such as the power of the laser light, the duration, repetitions, pulse shape, light wavelength, wavefront, as well as other relevant parameter.

The SLM treatment functionality 120 may use information from the planning functionality 118, and in particular the treatment locations and treatment parameters, to control the SLM device and possibly the therapeutic laser source. For example, the SLM planning functionality may generate the control signal to drive the SLM device that will cause the laser light to be delivered/focused according to the treatment plan.

FIG. 2 depicts a further ophthalmological system for delivering/focusing a treatment laser. The system 200 is similar to the system 100 and similar components will not be described in further detail. In addition to the optics for the therapeutic laser and SLM device, the system 200 is depicted as having an additional targeting laser source 250 and an imaging system 260. Although the system 200 is described as including both the targeting laser source and imaging system, it is possible for the system to incorporate only one of the components. Further, although depicted as a single imaging system, the system may include a plurality of different imaging systems and targeting systems. Canadian Patent Application 3,096,285 filed Oct. 16, 2020 and titled Ophthalmological Imaging And Laser Delivery Device, System and Methods" describes a device that can deliver a therapeutic laser and includes a number of imaging systems as well as a targeting laser. The entire contents of Canadian Patent Application 3,096,285 is incorporated herein by reference in its entirety for all purposes. The device described in Canadian Patent Application 3,096,285 uses scanning optics to allow the therapeutic laser to be delivered/focused at different locations. While the device described in Canadian Patent Application 3,096,285 can deliver/focus the therapeutic laser light at any desired treatment location, it cannot deliver/focus the therapeutic laser on multiple target locations simultaneously. By incorporating the SLM device for the therapeutic laser deliver, it is possible to modulate the phase of the therapeutic laser to deliver/focus the laser at multiple locations simultaneously.

As depicted, in addition to the therapeutic laser 102 and SLM device 106, the system 200 includes a targeting laser source 250 that passes through an optical pathway comprising various optical components 252 and a beam splitter/combiner 254 for combining the targeting laser with the therapeutic laser. The optical components 252 may include for example optical components and sensors for aligning the targeting laser so that its path is aligned with the path of the therapeutic laser once combined by the splitter combiner 254. The targeting laser light is modulated by the SLM device in the same manner as the therapeutic light; however, the targeting laser does not affect the biological ocular tissue. The targeting laser may have the same or different wavelengths as the therapeutic laser. If the wavelengths of the targeting and therapeutic lasers are different, the phase modulation can be digitally corrected. The targeting laser can act as a preview of where the therapeutic laser will actually be targeted and as such can be used to verify the treatment plan prior to actual treatment by the therapeutic laser.

The imaging system may comprise one or more systems for imaging the patient's eye 110 and may comprise respective light sources 262 which may include lasers and respective optical components 264 which may include lenses, scanning optics, splitters, combiners, etc. The imaging systems may include, for example a fundus imaging camera system, a scanning laser ophthalmoscopy (SLO) system, an optical coherence tomography (OCT) system or other imaging systems. One or more splitters/combiners 266 may be used to direct imaging light of each respective system from the imaging light source, to the eye and back to an imaging sensor of the particular imaging system. Separate imaging system may share one or more optical components.

Although not depicted in FIG. 2, the system 200 includes one or more controllers configured to provide system control functionality as described above. Control functionality may control the targeting laser as well as the imaging systems. The control functionality may control the system, including for example the SLM device 106, based on the information from the one or more imaging systems. For example, the imaging system may capture the location of the targeting laser delivered/focused by the SLM device. The actual locations of the delivered/focused targeting laser can be compared to the desired treatment locations, such as those locations provided by planning functionality and the results of the comparison used as feedback to control the SLM device and more precisely target the intended locations.

Further, one or more of the imaging systems may be used as an eye tracking system to track movements of the eye and update the targeting locations based on the movement. The control of the SLM device may be done in real time to adjust, for example at some frequency f, the delivery/focusing locations of the targeting laser and/or the therapeutic laser to account for eye movement.

FIG. 3 depicts a method of targeting a therapeutic laser on an ophthalmological target. The method 300 begins with determining targeting locations (302). The determination of the target locations may be done in various ways, including for example by displaying one or more images of a patient's eye and allowing an individual to specify the target locations on the images. Additionally or alternatively, the target locations may be determined automatically by processing images of the patient's eyes, such as for example using an artificially intelligent (AI) or machine learning (ML) algorithm or engine. The automatic or semi automatic determination of the targeting locations may include capturing images (318) such as fundus images, SLO images and/or OCT images, and processing the images by an AI engine trained to identify the target locations (320). The target locations may include the specific spatial location of the targets as well as treatment parameters for the particular location such as laser power, treatment repetitions, wavelength, pulse shape, etc. Regardless of how the target locations are determined, once they are determined, the SLM device is controlled in order to deliver/focus targeting laser on the determined locations (304). The targeting laser may be delivered/focused by the SLM device on the determined treatment locations; however, the targeting laser will not have the same parameters, such as the power, as the therapeutic laser. One or more images are captured that include the delivered/focused locations of the targeting laser (306). The captured images are processed to identify the actual targeted locations of the targeting laser and compare the captured locations to the determined treatment locations (308). Any discrepancy between the targeted locations and determined treatment locations can be used as feedback for controlling the SLM to more accurately target the treatment locations (310). As the SLM device is adjusted, additional images are captured of the targeting laser (312) and used to determine if the targeted locations are at acceptable locations relative to the desired treatment locations (314). If the targeted locations of the targeting lasers are not acceptable, (No at 314) the control of the SLM is again adjusted (310) and the targeting process continues. If the targeted locations are acceptable (Yes at 314), the treatment laser may be controlled (316) in order to treat the locations according to the treatment plan.

FIG. 4 depicts a further method of targeting a therapeutic laser on an ophthalmological target. The method 400 captures images (402) of a patient's eye. The images may be captured using a variety of different imaging techniques including a fundus camera, a SLO imaging system, an OCT imaging system or other imaging techniques. Two illustrative images 402a, 402b of a patient's eye are depicted in FIG. 4. The patient of image 402a has several microaneurysms and the patient of image 402b has glaucoma. Once the images are captures, they are processed to identify the treatment locations (404). The images 402a, 402b may be processed to identify locations requiring treatment as highlighted in FIGS. 404a, 404b. The treatment locations are highlighted in the figures with arrows. The identification of the treatment locations may be done manually, automatically, or semi-automatically requiring manual confirmation of the treatment locations. The treatment locations may be used to control the SLM device in order to shape the treatment laser beam to simultaneously be delivered to the target locations.

The SLM device may be controlled to deliver laser light simultaneously to the treatment locations (406). The treatment locations can be verified by first irradiating the locations with a targeting laser whose shape is adjusted by the SLM device. The locations that the targeting laser are delivered to can be captured by the imaging system and compared to the desired treatment locations. If the targeted locations are acceptable (Yes at 408), that is the targeting laser is delivered to the locations required to carry out the treatment, the treatment locations may be irradiated with the therapeutic laser (410), with the shape of the treatment laser being adjusted by the SLM device in order to be delivered to all of the treatment locations simultaneously. If the targeted locations are not acceptable, the SLM device can be controlled in order to adjust the treatment locations (412) and the adjusted treatment locations can again be irradiated by the targeting laser (406).

The above has described systems and methods that uses an SLM device to deliver/focus laser light to one or more locations within a patient's eye simultaneously. The SLM device is digitally controllable to impart some form of spatial phase modulation to light passing through or reflecting off the SLM device. The spatial phase modulation provided by the SLM device allows the shape of the laser light to be controlled to deliver/focus the laser light to multiple locations of the eye simultaneously. The SLM device may be provided by different types of devices, including for example translucent or transmissive SLM devices or reflective SLM devices. Translucent or transmissive SLM devices may be provided using liquid crystal display (LCD) technology while reflective SLM devices may be provided using liquid crystal on silicon (LCoS) technology. Other techniques for providing SLM devices capable of controllably imparting some spatial modulation to light may be used including for example a microelectromechanical micromirror-based SLM device, a membrane mirror-based SLM device as well as an active or a passive metasurface. Regardless of the type of SLM device, the laser light may be delivered/focused to different areas of the eye including, the sclera, iris, pupil, cornea, retina, vitreous humor, or other areas. The delivery/focusing of the laser light may be used to treat various eye conditions, including for example diabetic retinopathy, age-related macular degeneration, vitreomacular traction, tears, retinal detachments, holes, glaucoma, vein occlusion, choroidal detachment, diabetic macular edema, posterior vitreous detachment, cataract, floaters, and dry eye.

It will be appreciated by one of ordinary skill in the art that the system and components shown in FIGS. 1-4 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

Although certain components and steps have been described, it is contemplated that individually described components, as well as steps, may be combined together into fewer components or steps or the steps may be performed sequentially, non-sequentially or concurrently. Further, although described above as occurring in a particular order, one of ordinary skill in the art having regard to the current teachings will appreciate that the particular order of certain steps relative to other steps may be changed. Similarly, individual components or steps may be provided by a plurality of components or steps. One of ordinary skill in the art having regard to the current teachings will appreciate that the components and processes described herein may be provided by various combinations of software, firmware and/or hardware, other than the specific implementations described herein as illustrative examples.

The techniques of various embodiments may be implemented using software, hardware and/or a combination of software and hardware. Various embodiments are directed to apparatus, e.g. a node which may be used in a communications system or data storage system. Various embodiments are also directed to non-transitory machine, e.g., computer, readable medium, e.g., ROM, RAM, CDs, hard discs, etc., which include machine readable instructions for controlling a machine, e.g., processor to implement one, more or all of the steps of the described method or methods.

Some embodiments are directed to a computer program product comprising a computer-readable medium comprising code for causing a computer, or multiple computers, to implement various functions, steps, acts and/or operations, e.g. one or more or all of the steps described above. Depending on the embodiment, the computer program product can, and sometimes does, include different code for each step to be performed. Thus, the computer program product may, and sometimes does, include code for each individual step of a method, e.g., a method of operating a communications device, e.g., a wireless terminal or node. The code may be in the form of machine, e.g., computer, executable instructions stored on a computer-readable medium such as a RAM (Random Access Memory), ROM (Read Only Memory) or other type of storage device. In addition to being directed to a computer program product, some embodiments are directed to a processor configured to implement one or more of the various functions, steps, acts and/or operations of one or more methods described above. Accordingly, some embodiments are directed to a processor, e.g., CPU, configured to implement some or all of the steps of the method(s) described herein. The processor may be for use in, e.g., a communications device or other device described in the present application.

Numerous additional variations on the methods and apparatus of the various embodiments described above will be apparent to those skilled in the art in view of the above description. Such variations are to be considered within the scope.

We claim:

1. A therapeutic laser delivery system, the system comprising:

a therapeutic laser configured to generate a therapeutic laser light for passing through a therapeutic laser delivery optical path;

a spatial light modulator (SLM) device arranged in the therapeutic laser delivery optical path and configured to modulate the therapeutic laser light to:

split the therapeutic laser light into a plurality of therapeutic laser light beams; and simultaneously deliver the plurality of therapeutic laser light beams to a plurality of target locations in an eye, wherein the SLM device is configurable to control modulation of the therapeutic laser light and the plurality of target locations of the eye that the plurality of therapeutic laser light beams is simultaneously delivered to;

a targeting laser configured to generate a targeting laser light for passing through a targeting laser delivery optical path, wherein the SLM device is arranged in the targeting laser delivery optical path and further configured to modulate the targeting laser light into a plurality of targeting laser light beams, and wherein the SLM device is configurable to control modulation of the therapeutic laser light in order to correct for a difference between a target location of the plurality of target locations and a determined treatment location; and a processor for executing software instructions to configure the SLM device and set the plurality of target locations of the eye that the plurality of therapeutic laser light beams is simultaneously delivered to.

2. The system of claim 1, wherein the therapeutic laser delivery optical path is aligned with the targeting laser delivery optical path.

3. The system of claim 1, further comprising an imaging system for capturing an image of the eye.

4. The system of claim 3, wherein the imaging system comprises one or more of:

a fundus camera system;

a scanning laser ophthalmoscopy (SLO) imaging system; and an optical coherence tomography (OCT) system.

5. The system of claim 1, further comprising:

a targeting laser configured to generate a targeting laser light for passing through a targeting laser delivery optical path, wherein the SLM device is arranged in the targeting laser delivery optical path and further configured to modulate the targeting laser light to:

split the targeting laser light into a plurality of targeting laser light beams and simultaneously deliver the plurality of targeting laser light beams to the plurality of target locations; and an imaging system for capturing an image of the eye while the SLM device simultaneously delivers the plurality of targeting laser light beams to the plurality of target locations of the eye, wherein the processor is further configured to execute software instructions to process the captured image to compare the plurality of targeting laser light beams delivered by the SLM device to the plurality of target locations.

6. The system of claim 5, wherein the processor is further configured to execute software instructions to, based on the processing of the captured image, reconfigure the SLM device and update the plurality of target locations of the eye that the plurality of therapeutic laser light beams are simultaneously delivered to.

7. The system of claim 5, wherein the comparison of the plurality of targeting laser light beams captured in the image to the plurality of target locations is used as feedback for controlling the SLM device.

8. A therapeutic laser delivery system, the system comprising:

a therapeutic laser configured to generate a therapeutic laser light for passing through a therapeutic laser delivery optical path;

a spatial light modulator (SLM) device arranged in the therapeutic laser delivery optical path and configured to modulate the therapeutic laser light to:

adapt one or more characteristics of the therapeutic laser light for increased coverage of or application to floaters in a vitreous humour of an eye, the one or more characteristics being at least one of: a shape, a lightwave phase, a lightwave polarization, a wavefront tilt, a diffraction, a wavefront helicity, and an orbital angular momentum order, wherein the SLM device is configurable to control modulation of the therapeutic laser light; and a processor for executing software instructions to configure the SLM device and set the adapting of the one or more characteristics of the therapeutic laser light.

9. The system of claim 8, further comprising an imaging system for capturing an image of the eye, wherein the imaging system comprises one or more of:

a fundus camera system;

a scanning laser ophthalmoscopy (SLO) imaging system; and an optical coherence tomography (OCT) system.

10. A method of using a therapeutic laser delivery system to simultaneously treat multiple locations in an eye, wherein the method comprises:

determining target locations in the eye to simultaneously receive light for treating an ocular condition; and executing software instructions on a processor of the therapeutic laser delivery system to configure a spatial light modulator (SLM) device of the therapeutic laser delivery system to simultaneously deliver therapeutic laser light beams to the determined target locations, wherein the therapeutic laser delivery system comprises:

a therapeutic laser configured to generate a therapeutic laser light for passing through a therapeutic laser delivery optical path;

a targeting laser configured to generate a targeting laser light for passing through a targeting laser delivery optical path;

the spatial light modulator (SLM) device arranged in the therapeutic laser delivery optical path and the targeting laser delivery optical path and configured to modulate received laser light to:

split the received laser light into a plurality of laser light beams; and simultaneously deliver the plurality of laser light beams to a plurality of target locations in the eye, wherein the SLM device is configurable to control modulation of the received laser light and the plurality of target locations of the eye that the plurality of laser light beams are simultaneously delivered to; and the processor for executing software instructions to configure the SLM device and set the plurality of target locations of the eye that the plurality of laser light beams are simultaneously delivered to;

operating the targeting laser to generate the targeting laser light; and controlling the SLM device to modulate the targeting laser light to split the targeting laser light into a plurality of targeting laser light beams to be simultaneously delivered to the determined-target locations.

11. The method of claim 10, further comprising:

operating the therapeutic laser to generate the therapeutic laser light; and controlling the SLM device to modulate the therapeutic laser light to split the therapeutic laser light into the plurality of therapeutic laser light beams and simultaneously deliver the therapeutic laser light beams to the determined target locations.

12. The method of claim 10, further comprising:

capturing an image of the plurality of targeting laser light beams being simultaneously delivered to the plurality of target locations set;

comparing, based on the image captured, the plurality of target locations set that the plurality of targeting laser light beams were delivered to against the determined-target locations; and reconfiguring the SLM device to update the plurality of target locations in the eye that the SLM device simultaneously delivers laser light beams to.

13. The method of claim 12, further comprising:

operating the therapeutic laser to generate the therapeutic laser light; and controlling the SLM device to modulate the therapeutic laser light to split the therapeutic laser light into the plurality of therapeutic laser light beams to be simultaneously delivered to the determined-target locations.

14. The method of claim 12, wherein the processor is further configured to execute software instructions to, based on the comparing, reconfigure the SLM device and update the plurality of target locations of the eye that the plurality of therapeutic laser light beams are simultaneously delivered to.

15. The method of claim 10, wherein determining target locations in the eye comprises:

capturing one or more images of the eye; and processing the one or more images to determine the target locations.

16. The method of claim 10, wherein the therapeutic laser delivery optical path is aligned with the targeting laser delivery optical path.

17. The method of claim 10, wherein the therapeutic laser delivery system further comprises an imaging system for capturing an image of the eye.

18. The method of claim 17, wherein the imaging system comprises one or more of:

a fundus camera system;

a scanning laser ophthalmoscopy (SLO) imaging system; and an optical coherence tomography (OCT) system.

19. The method of claim 10, wherein the SLM device comprises one or more of:

a liquid crystal-based SLM device;

a microelectromechanical micromirror-based SLM device;

a membrane mirror-based SLM device;

an active metasurface; and a passive metasurface.

* * * * *